(12) United States Patent
Witte et al.

(10) Patent No.: US 9,676,026 B2
(45) Date of Patent: Jun. 13, 2017

(54) IMPLANT MADE OF A MAGNESIUM ALLOY AND METHOD FOR THE PRODUCTION THEREOF

(71) Applicant: AAP IMPLANTATE AG, Berlin (DE)

(72) Inventors: Frank Witte, Hannover (DE); Norbert Hort, Luneburg (DE); Marco Wolfstadter, Worth/Main (DE); Bernd Frohlich, Baunatal (DE); Wolfgang Voith, Aldingen (DE); Hans-Joachim Fischer, Berlin (DE)

(73) Assignee: AAP Implantate AG, Berlin (DE)

( * ) Notice: Subject to any disclaimer, the term of this patent is extended or adjusted under 35 U.S.C. 154(b) by 0 days.

(21) Appl. No.: 14/529,545

(22) Filed: Oct. 31, 2014

(65) Prior Publication Data

US 2015/0053364 A1 Feb. 26, 2015

Related U.S. Application Data

(62) Division of application No. 13/058,573, filed as application No. PCT/EP2009/005818 on Aug. 11, 2009, now abandoned.

(30) Foreign Application Priority Data

Aug. 11, 2008 (DE) .................. 10 2008 037 200

(51) Int. Cl.
*B22D 17/00* (2006.01)
*B22D 25/02* (2006.01)
(Continued)

(52) U.S. Cl.
CPC .......... *B22D 25/02* (2013.01); *A61B 17/0401* (2013.01); *A61B 17/8052* (2013.01);
(Continued)

(58) Field of Classification Search
CPC ........ B22D 17/00; B22D 21/00; B22D 25/02; B22D 25/06
(Continued)

(56) References Cited

U.S. PATENT DOCUMENTS 6,874,562 B2 4/2005 Knott et al.
2002/0121157 A1* 9/2002 Knott et al. ......... B22D 25/005
75/392

(Continued)

FOREIGN PATENT DOCUMENTS

EP 0875218 11/1998
WO WO 2005065576 7/2005
(Continued)

OTHER PUBLICATIONS

Staiger et al., Magnesium and its alloys as orthopedic biomaterials: a review, Biomaterials, 2006, 1728-1734, 27.
(Continued)

*Primary Examiner* — Kevin P Kerns
(74) *Attorney, Agent, or Firm* — Pearl Cohen Zedek Latzer Baratz LLP

(57) ABSTRACT

A method for manufacturing a bioresorbable implant, wherein a magnesium alloy is formed into an implant. A melt is pressed into a die and gases in the die induce turbulence in the inflowing melt, thereby enclosing gas, so that the porous implant is formed with a porosity, which increases from outside inwardly. The surface of the implant is substantially free from open pores.

13 Claims, 5 Drawing Sheets

(51) Int. Cl.
| | |
|---|---|
| *B22D 25/06* | (2006.01) |
| *A61B 17/04* | (2006.01) |
| *A61B 17/80* | (2006.01) |
| *A61B 17/86* | (2006.01) |
| *A61L 27/04* | (2006.01) |
| *A61L 27/56* | (2006.01) |
| *A61L 31/02* | (2006.01) |
| *A61L 31/14* | (2006.01) |
| *B22D 21/00* | (2006.01) |
| *A61B 17/00* | (2006.01) |
| *A61F 2/30* | (2006.01) |

(52) U.S. Cl.
CPC .......... *A61B 17/864* (2013.01); *A61B 17/866* (2013.01); *A61L 27/047* (2013.01); *A61L 27/56* (2013.01); *A61L 31/022* (2013.01); *A61L 31/146* (2013.01); *A61L 31/148* (2013.01); *B22D 17/00* (2013.01); *B22D 21/007* (2013.01); *B22D 25/06* (2013.01); *A61B 2017/00004* (2013.01); *A61B 2017/00212* (2013.01); *A61B 2017/00411* (2013.01); *A61B 2017/044* (2013.01); *A61B 2017/0412* (2013.01); *A61B 2017/0414* (2013.01); *A61B 2017/0437* (2013.01); *A61B 2017/0445* (2013.01); *A61B 2017/0459* (2013.01); *A61F 2002/30062* (2013.01); *A61F 2210/0004* (2013.01); *A61F 2250/0023* (2013.01); *A61F 2250/0024* (2013.01); *A61F 2310/00041* (2013.01)

(58) Field of Classification Search
USPC ........................................................ 164/113
See application file for complete search history.

(56) References Cited

U.S. PATENT DOCUMENTS

| | | | |
|---|---|---|---|
| 2003/0049150 | A1 | 3/2003 | Singer et al. |
| 2004/0094284 | A1* | 5/2004 | Sambrook ............. B22D 19/14 164/98 |
| 2005/0238690 | A1 | 10/2005 | Li et al. |
| 2006/0167147 | A1* | 7/2006 | Asgari ................. A61K 9/0024 524/174 |
| 2006/0271168 | A1 | 11/2006 | Kleine et al. |
| 2008/0161906 | A1 | 7/2008 | Atanasoska et al. |

FOREIGN PATENT DOCUMENTS

| | | |
|---|---|---|
| WO | WO 2007016796 | 2/2007 |
| WO | WO 2007125532 | 11/2007 |

OTHER PUBLICATIONS

DTI Global Watch Mission Report, MagTech1: magnesium alloys and processing technologies for lightweight transport applications—a mission to Europe, Sep./Oct. 2004, pp. 1-24.

* cited by examiner

IMPLANT MADE OF A MAGNESIUM ALLOY AND METHOD FOR THE PRODUCTION THEREOF

CROSS-REFERENCE TO RELATED APPLICATIONS

This application is a division of U.S. patent application Ser. No. 13/058,573, filed Sep. 9, 2011, now abandoned, which is a U.S. national stage of PCT/EP2009/005818 filed Aug. 11, 2009, which claims priority to and the benefit of German Application No. 10 2008 037 200.5 filed on Aug. 11, 2008, the contents of which are incorporated herein by reference.

FIELD OF THE INVENTION

Background of the Invention

Bioresorbable implants, in particular implants from magnesium or a magnesium alloy, are known. Especially, magnesium is known to have a positive effect on the healing of bones and to slowly decompose in the body such that bioresorbable implants can be manufactured using magnesium.

In particular, screws, wires, pins etc. are known which are substantially made of magnesium.

A disadvantage of prior magnesium implants is that as soon as an implant is degraded into a small depth the mechanical properties of the implant, in particular screws, are impaired in a degree that the implant loses its mechanical effect. The remaining residual implant, i.e. the core of the implant, then rests in the body and is subjected to a rather long decomposition process, since each of further corrosive attacks only occurs at the surface.

A further disadvantage of prior magnesium implants is that manufacturing of the implant employing machining techniques is difficult. Machining processes of magnesium alloys always imply a high risk of fire. Manufacturing, therefore, always has to be performed with appropriate care and hence is time consuming and complex.

OBJECT OF THE INVENTION

An object of the invention, therefore, is to provide an implant which has improved properties in view of a successful therapy, and which can be produced in a simple way.

Another object of the invention is to provide an implant, which maintains its mechanical properties for a relatively long period during the decomposition process, i.e. the decomposition process of the residual implant which anyway has lost its function takes an as low fraction of the whole retention time in the body as possible.

A further object of the invention is to reduce the mass of bioresorbable material that has to be decomposed in the body.

Another object of the invention is to provide a magnesium alloy for medical applications which has a high tolerance and good mechanical properties.

A particular object of the invention is to reduce the proportion of zinc which, when over-dosed, may provoke inflammations in the body, but is used for ameliorating the mechanical properties of magnesium alloys.

SUMMARY OF THE INVENTION

The object of the invention is already solved by an implant from magnesium or a magnesium alloy, and by a magnesium alloy for an implant according to any of the independent claims.

Preferred embodiments and modifications of the invention are set forth in the respective dependent claims.

The invention, according to one aspect, relates to an implant of magnesium die-casting or a magnesium die cast alloy, the implant being porous, at least in portions thereof, and porosity increases from outside inwardly, at least in portions thereof. Thus, according to the invention porosity increases from the surface(s) of the implant towards the core of the implant. A result of this is that the decomposition process is retarded at the less porous surface as opposed to the core of the implant. Hence, following placement of the implant decomposition starts relatively slowly, but once the regions close to the surface have been decomposed the remaining residual core of the implant is given way to fast decomposition. The surface, in contrast, preferably has a casting skin which retards corrosive attack in an initial period following placement.

Thus, the implant maintains its minimal required mechanical properties over a relatively longer period of the total decomposition process.

In a preferred embodiment of the invention, the surface of the implant is substantially free of open pores; in particular the surface has less than 3 open pores of a diameter of more than 100 $\mu m/cm^2$.

The inventors have found that already a relatively low porosity results in a surprisingly strongly accelerated decomposition process. With a closed, substantially pore-free surface, however, the decomposition process starts with a high retardation.

In another preferred embodiment of the invention the implant is formed such that the textural structure, i.e. the mean grain diameter of an at least partially crystalline alloy becomes coarser in the inward direction, i.e. towards the core. A larger grain size also seems to involve faster decomposition in the body.

Preferably, the porosity in a first region close to the surface which for example is defined into a maximum depth of 0.5 mm, is less than 3%, most preferably less than 2%.

In a region away from the surface which particularly can be defined by a depth of more than 0.6 mm as seen from the surface, the degree of porosity is preferably more than 3%, most preferably more than 5%. The term porosity herein refers to closed porosity, i.e. the ratio of open and closed pores. The degree of porosity of the implant can be from 1 to 40%, preferably from 2 to 8%.

Porosities of up to about 40% are technically feasible. It has been found, however, that already relatively small degrees of porosity, in particular more than 3%, considerably accelerate the decomposition process of the remaining residual implant.

In a modification of the invention, the implant comprises a magnesium alloy having an amount of yttrium from 0.5 to 10% (% amounts are in wt-%, unless otherwise stated), preferably from 1 to 9% and most preferably from 3 to 5%. Yttrium serves as an additive primarily for retarding corrosion of the implant. Thus, the amount of yttrium allows to set the desired useful life of the implant until the same loses its properties due to decomposition.

Preferably, the magnesium alloy comprises an amount of other rare earths, i.e., rare earth metals besides yttrium, of less than 2%, more preferably less than 1%.

In a preferred embodiment of the invention, an amount of the elements Gd, Tb, Dy, Ho, Er, Tm, Yb, and Lu in the alloy, which exhibit high solubility, is less than 0.4% each, and less than 0.7% in total.

In a preferred embodiment of the invention, an amount of the elements Nd, La, Ce, Pr, Sm, and Eu, which exhibit a relatively high solubility, is less than 0.15% each, and less than 0.4% in total.

In this way, an alloy is provided which exhibits a homogeneous precipitation behavior during casting.

For preventing partially undesirable side effects, the implant preferably has an amount of at least one of elements Al, Zn, Si, Mn, Ca, Zr, Li, Sn, Sr, and P of less than 0.2% each, and less than 0.4% in total.

Moreover, the implant preferably comprises less than 50 ppm of each of the elements Ag, Au, Cu, Fe, and Ni.

An alternative embodiment of the invention, however, contemplates to add silver, in particular in atomic or nano-particle form, to obtain antiseptic properties, depending on the indication.

The amount of beryllium preferably is less than 4 ppm.

In a modification of the invention, the implant is coated, at least in portions thereof.

For instance it is contemplated to employ a coating which is similarly bioresorbable, i.e. degrades in the body.

Especially biocompatible polymers, slowly dissolving oxide layers, or degradable coatings from hydroxyapatite or other calcium phosphate salts are provided.

Coatings of polymers such as poly-L-lactic acid, polycaprolactone or fluoride coatings also dissolve within a specific residence time.

In an initial period following the placement of the implant, a coating can virtually completely prevent degradation. Thus, the implant retains its mechanical properties during an initial period.

In another embodiment of the invention, a coating is used which decomposes or dissolves at a temperature above the body temperature. Thus, it is conceivable to inductively heat an implant that has been placed to a temperature between 40° C. and 60° C. whereby the coating is decomposed and exposes the remaining magnesium implant for decomposition.

In a modification of the invention, the implant has a blasted surface. In this way, burrs can be removed. On the other hand, blasting can result in compaction of the surface, thereby retarding the initial decomposition process.

In a preferred embodiment of the invention the implant is formed in one piece.

A die cast process has turned out to be particularly useful as a manufacturing method for implants according to the invention.

The inventors have found that a die cast process allows to provide implants with a porous core but a substantially pore-free surface in a very economical way.

The melt is compressed in a die under high pressure. Here, the die preferably is not evacuated as is the case in some vacuum assisted die cast processes. The gases which are in present the die induce turbulences of the inflowing melt thereby enclosing gas, in particular air, which results in a porosity of the implant while the surface of the implant remains substantially free of pores and closed.

During the die cast process the melt is compressed in the die under a high pressure, in particular more than 20, preferably more than 100 bars.

It is preferred to process the melt in a very low viscosity condition, under high temperature. In particular, the casting temperature is above 600, preferably above 700° C.

In a preferred embodiment of the invention, the casting rate is more than 5, preferably more than 20 cm/s.

The inventors have found that high temperatures and high pressures allow to process alloys having a small amount of aluminum and, with the exception of yttrium, a small amount of rare earths.

In contrast to prior die cast methods for non-medical applications, the poorer flow behavior of the alloy preferably used results in a formation of porous structures within the implant. Such porous structures that absolutely have to be avoided in non-medical applications result in the improved properties of the bioresorbable implant as described above.

Besides removal of burrs such as by blasting it is, alternatively or additionally, possible to deburr the implant by igniting an explosion in a drum in which the implant is positioned.

The invention is useful for providing implants for various applications, in particular screws, suture anchors, i.e. anchors which serve to fix sutures, and for suture wound anchors, i.e. an anchor arrangement for fixing soft tissue to bones.

The invention further relates to a magnesium alloy for an implant, in particular a magnesium die cast alloy. The magnesium alloy has an amount of 1 to 9% of yttrium, and between 0.1 and 1.5% of other rare earth metals, with an amount of zinc of less than 0.4%.

The inventors have found that by an appropriate choice of rare earth metals in addition to yttrium, the mechanical properties can be adapted such that the implant has a sufficient strength without adding zinc. Also, a large amount of Al and further rare earth metals can be dispensed with. Therefore, the alloy is well tolerated.

In particular, a magnesium alloy is provided which comprises the following additional ingredients: Gd, Tb, Dy, Ho, Er, Tm, Yb, and Lu in an amount of less than 0.4% each, between 0.1 and 0.7% in total; Nd, La, Ce, Pr, Sm, and Eu in an amount of less than 0.15% each, between 0.05 and 0.3% in total; Al, Zn, Si, Mn, Ca, Zr, Li, Sn, Sr, and P in an amount of less than 0.2% each, between 0.05 and 0.3% in total; Ag, Au, Cu, Fe, and Ni in an amount of less than 50 ppm each; less than 4 ppm of Be.

In this way, a crystalline die cast alloy with grain sizes between 2 and 2000 µm can be provided. In particular, a micro-crystalline die cast alloy can be provided.

The magnesium alloy of the invention attains a yield strength $R_{p0.2}$ of more than 70, preferably more than 75 MPa.

The tensile strength $R_m$ is more than 90, preferably more than 100 MPa, the breaking elongation A is more than 3%.

The invention further relates to an implant from magnesium or a magnesium alloy, the implant being coated, at least in portions thereof.

Thus, the implant comprises a biodegradable core from magnesium or a magnesium alloy which is only subjected to degradation after the coating has been released or melted off. In this way, the implant retains its mechanical properties for a relatively long period after its placement. The core is preferably porous, at least portions thereof, which considerable promotes degradation once the coating is no longer present.

As a coating, biocompatible polymers as mentioned above are provided, e.g. poly-L-lactic acid, polycaprolactone, slowly dissolving oxide layers, or degradable coatings from hydroxyapatite or other calcium phosphate salts.

In a modification of the invention the implant has a coating, at least portions thereof, which decomposes or dissolves at a temperature above the body temperature. This is in particular a polymeric coating, especially of a polyethylene oxide or polylactide.

Heating may be achieved from the outside, for example by means of electromagnetic waves, in particular radio or microwave energy, by induction, or by introducing ultrasonic energy.

In order to prevent damage of the adjacent tissue, the coating preferably has a melting temperature from 20 to 60° C.

DESCRIPTION OF THE DRAWINGS

The invention will now be described in detail with reference to the drawings of FIG. 1 to FIG. 10.

Figure 1:
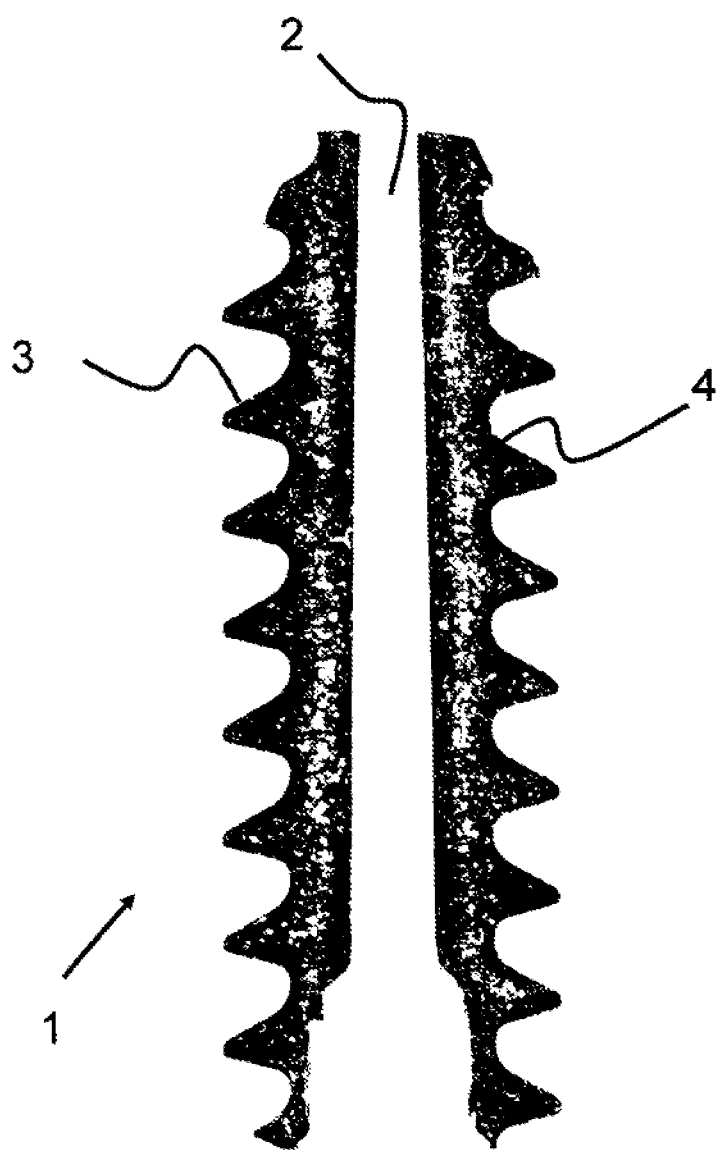
FIG. 1 schematically shows a section through an implant 1, here in form of an interference screw. The interference screw of this exemplary embodiment has a central passage 2.

Implant 1 is produced by a die cast method from a magnesium alloy and has a surface 3 which is substantially free of pores and closed.

Interiorly, i.e. in a region 4 away from the surface, implant 1 has a considerably higher porosity than at the surface 3.

Since passage 2 is not defined by drilling but already by the casting die, the surface of passage 2 is equally free of pores and closed.

Following placement of the implant in the body, the decomposition rate at surface 3 of the implant is considerably reduced compared to the decomposition rate in a core 4 of the implant.

In this way, an implant can be provided which maintains its required mechanical properties for a relatively long period.

The implant 1 can have a coating (not shown) which substantially prevents degradation of the implant 1 following placement in the body. The coating can be melted away at a later time by application of electromagnetic waves, or by induction. In this way, the mounted implant is uncovered and subjected to degradation.

Figure 2:
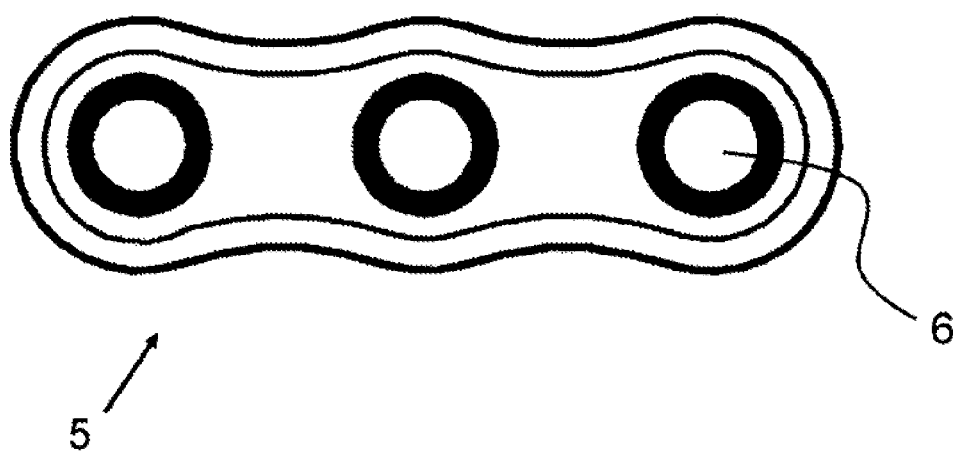

FIG. 2 schematically shows a plate 5 which is used, for example, for joining bone fragments.

For fixing, the plate 5 has at least threads 6 or alternatively a drilling hole, through which a screw is threaded into the bone.

Thread 6 is preferably formed during die casting by means of a threaded pin which is introduced into the casting die and which is threaded out upon ejection of plate 5. In this way, the surface of thread 6 also has a casting skin. Alternatively, thread 6 can be cut. In fact, this destroys the casting skin; following placement, however, thread 6 is protected by a screw.

Figure 3:
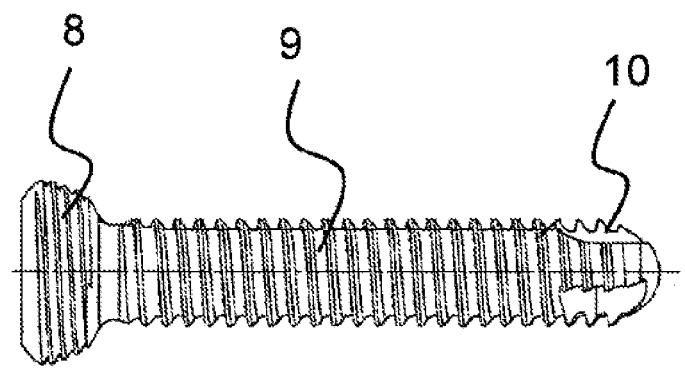

FIG. 3 schematically shows a screw 7 which, e.g., may serve for fixing the plate illustrated in FIG. 2. This represents an angularly stable system wherein head 8 of the screw 7 has an external thread for engaging the thread of the plate. Screw body 9 is provided with a thread for threading into the bone, the thread having a self-cutting portion 10 at the tip.

Figure 4:
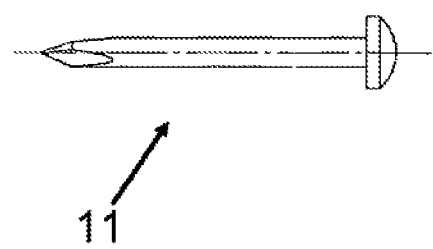

FIG. 4 schematically shows a pin 11 which is placed by means of an appropriate tool. This pin, too, is produced in a die cast process and is interiorly porous. Pin 11 is especially intended for smaller fractures.

Figure 5:
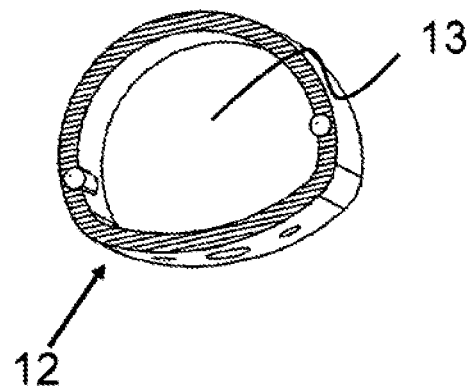

FIG. 5 shows a cage 12 for stiffening vertebral bodies. Cage 12 consists of a substantially tubular portion which is filled with bone granules in its interior 13. The bone granules cause generation of bone such that after degradation of the portion made from a magnesium alloy the vertebral bodies are grown together.

Figure 6:
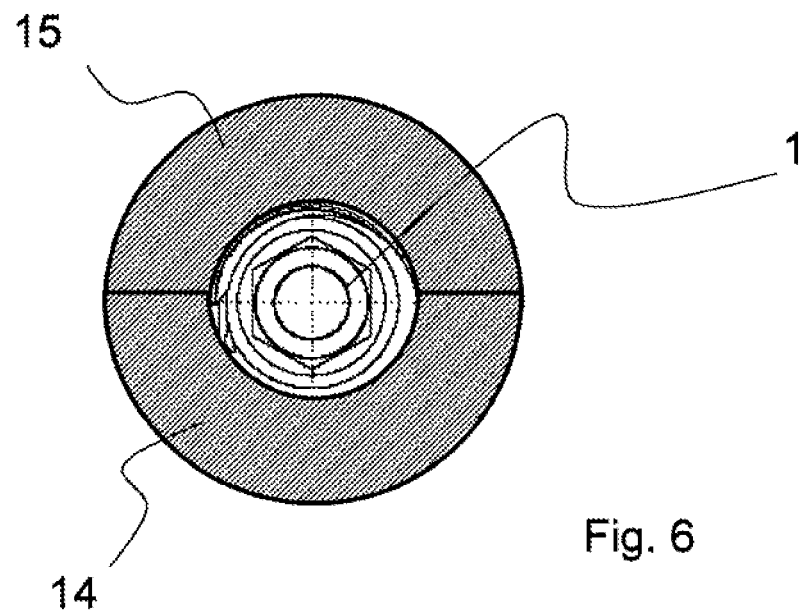
Figure 7:
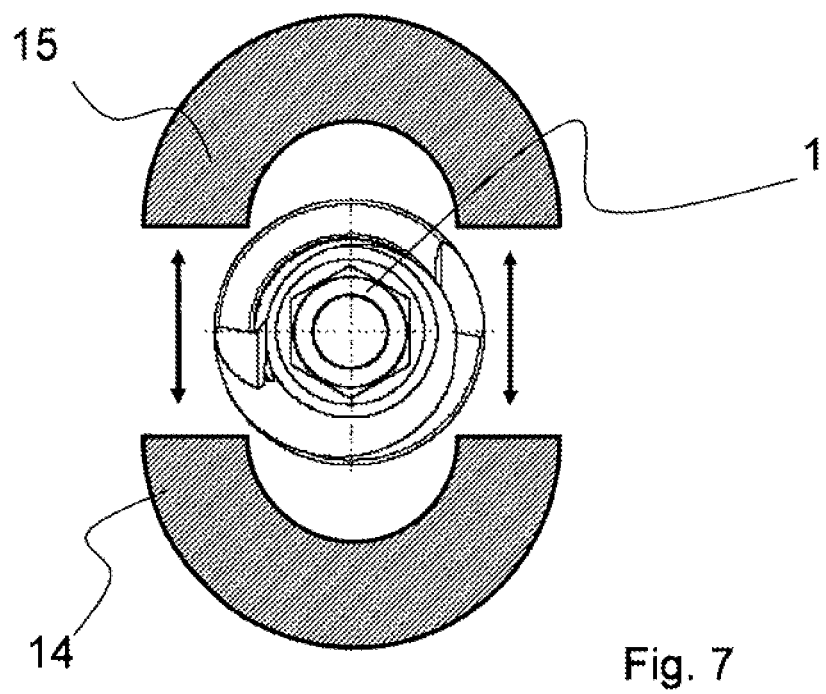

With reference to FIGS. 6 and 7, a method for manufacturing an implant 1 will be described.

FIG. 7 illustrates a sectional view of a casting die which comprises an upper portion 15 and a lower portion 14. A magnesium alloy comprising an amount of yttrium is compressed in this die under high temperature and high pressure. The melt solidifies within fractions of a second. In this way, a fine-grained casting skin is formed at the surface of implant 1, while inside the implant a porous structure with a coarser texture is formed, assumable due to turbulences and the relatively poor flow behavior of the alloy used.

Subsequently, as depicted in FIG. 7, the die comprised of upper portion 15 and lower portion 14 is opened and the implant is ejected.

It will be understood that the die is depicted in fairly schematic manner and that in practical use it will comprise other portions and components. In particular, a die is contemplated which comprises at least four parts.

Figure 8:
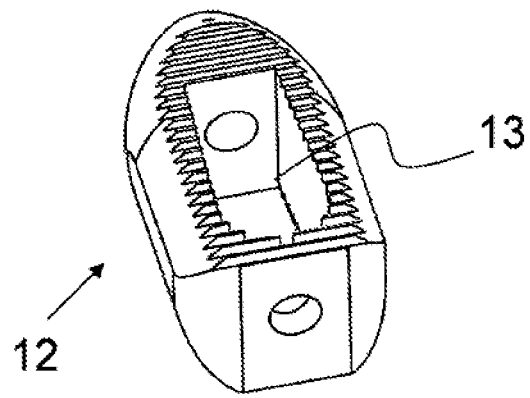

FIG. 8 shows an alternative embodiment of a cage 12 which is adapted to be placed in the cervical spine. This cage 12 also has an opening 13 which can be filled with bone granules.

Figure 9:
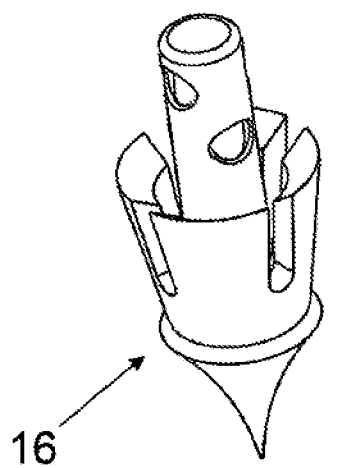
Figure 10:
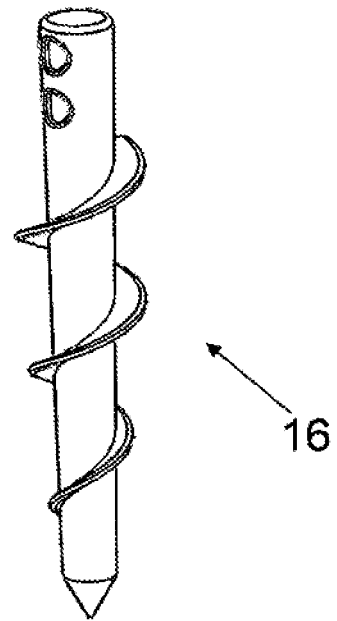

FIG. 9 and FIG. 10 show different embodiments of a suture anchor 16.

The invention claimed is:

1. A method for manufacturing a bioresorbable implant, comprising pressing a magnesium alloy melt into a high pressure casting die without first evacuating the die, so that porosity in the implant is produced solely from air in the die inducing turbulence in and being enclosed in the melt, so that a porous implant is formed with a porosity which increases from outside inwardly, and which has a surface which is substantially free of open pores.

2. The method of claim 1, wherein the magnesium alloy comprises from about 1 to about 9% of Y, and from about 0.1 to about 1.5% of other rare earth metals.

3. The method of claim 1, wherein the pressure under which the melt is compressed in the die during a die casting process is more than about 100 bars.

4. The method of claim 1, wherein a casting temperature is above about 600° C.

5. The method of claim 1, wherein a casting rate more than about 20 cm/s is used.

6. The method of claim 1, wherein the implant is formed in a form selected from the group consisting of: a screw, a cage, a suture anchor, and a suture wound anchor.

7. The method of claim 1, wherein the magnesium alloy comprises from about 1 to about 9% of Y and between from about 0.1 and to about 1.5% of other rare earth metals, and wherein the amount of Zn is less than about 0.4%.

8. The method of claim 1, wherein a closed surface retards corrosive attack in an initial period following placement.

9. The method of claim 1, wherein the surface is formed which has less than 3 open pores with a diameter of more than 100 µm/cm2.

10. The method of claim 1, wherein a degree of porosity in a first region close to the surface is less than 3%.

11. The method of claim 10, wherein the region close to the surface is defined by a maximum depth of 0.5 mm.

12. The method of claim 10, wherein the degree of porosity in a second region, away from the surface, is more than 3%.

13. The method of claim 12, wherein the second region away from the surface is defined by a depth of more than 0.6 mm.

* * * * *